United States Patent
Zhang et al.

(10) Patent No.: US 11,325,953 B2
(45) Date of Patent: May 10, 2022

(54) PROTEIN OF 'DANGSHAN SULI' HAVING FUNCTION OF PROMOTING GROWTH OF POLLEN TUBE, ENCODING GENE PBRTTS1 AND USE THEREOF

(71) Applicant: NANJING AGRICULTURAL UNIVERSITY, Nanjing (CN)

(72) Inventors: Shaoling Zhang, Nanjing (CN); Huijun Jiao, Nanjing (CN); Juyou Wu, Nanjing (CN); Linlin Xu, Nanjing (CN); Xiaosan Huang, Nanjing (CN); Zhihua Xie, Nanjing (CN); Qian Liu, Nanjing (CN); Yaojun Chang, Nanjing (CN); Peng Wang, Nanjing (CN)

(73) Assignee: Nanjing Agricultural University, Nanjing (CN)

( * ) Notice: Subject to any disclaimer, the term of this patent is extended or adjusted under 35 U.S.C. 154(b) by 218 days.

(21) Appl. No.: 16/448,209

(22) Filed: Jun. 21, 2019

(65) Prior Publication Data
US 2020/0048314 A1    Feb. 13, 2020

(30) Foreign Application Priority Data
Jun. 21, 2018 (CN) .......................... 201810642892.3

(51) Int. Cl.
 C07K 14/415 (2006.01)
 C12P 19/34 (2006.01)
 A01H 1/02 (2006.01)

(52) U.S. Cl.
 CPC .............. *C07K 14/415* (2013.01); *A01H 1/02* (2013.01); *C12P 19/34* (2013.01)

(58) Field of Classification Search
 None
 See application file for complete search history.

(56) References Cited

PUBLICATIONS

Sequence Accession FX620234, Jan. 8, 2014, attached to the office action. (Year: 2014).*

* cited by examiner

*Primary Examiner* — Elizabeth F McElwain
(74) *Attorney, Agent, or Firm* — Avek IP, LLC

(57) ABSTRACT

Some embodiments of the disclosure provide a protein for promoting the growth of a pollen tube and a gene PbrTTS1 encoding the protein. The amino acid sequence of the protein is shown in SEQ ID No: 1. The nucleotide sequence of the gene PbrTTS1 encoding the protein is shown in SEQ ID No: 2. Other embodiments of the disclosure provide a primer for amplifying the gene PbrTTS1 encoding the protein. The primer includes a forward primer and a reverse primer. The nucleotide sequence of the forward primer is shown in SEQ ID No: 3, and the nucleotide sequence of the reverse primer is shown in SEQ ID No: 4.

7 Claims, 8 Drawing Sheets

Specification includes a Sequence Listing.

FIG. 3

SEQUENCE LISTING

```
<160> NUMBER OF SEQ ID NOS: 31

<210> SEQ ID NO 1
<211> LENGTH: 193
<212> TYPE: PRT
<213> ORGANISM: Artificial Sequence
<220> FEATURE:
<223> OTHER INFORMATION: A protein of 'Dangshan Suli' for promoting the
      growth of a pollen tube of 'Dangshan Suli'

<400> SEQUENCE: 1

Met Gly Ser Pro Ala Val Phe Val Gln Leu Ser Val Leu Leu Leu Ser
1               5                   10                  15

Cys Phe Thr Val Phe Val His Pro Pro Ala His Ser Pro Val His Pro
            20                  25                  30

Pro Ala His Ser Pro Val His Pro Pro Ser Pro Pro His His His Gly
        35                  40                  45

His Pro Pro Val His Pro Pro Met Tyr Pro Pro Lys Lys Pro Phe Pro
    50                  55                  60

Arg Ser Phe Val Ala Val Gln Gly Val Val Tyr Cys Lys Ser Cys Asn
65                  70                  75                  80

Tyr Ser Gly Val Asp Thr Leu Asn Gly Ala Lys Pro Val Leu Gly Ala
                85                  90                  95

Thr Val Lys Leu Gln Cys Asn Asn Arg Lys Phe Pro Leu Val Val Lys
            100                 105                 110

Glu Thr Thr Asp Lys Asn Gly Tyr Phe Phe Ile Thr Ala Pro Lys Thr
        115                 120                 125

Ile Thr Thr Phe Gly Ala His Lys Cys Lys Val Ser Leu Val Ser Ser
    130                 135                 140

Pro Ser Ala Ala Cys Ser Lys Pro Ser Asp Leu His Gly Gly Leu Ser
145                 150                 155                 160
```

Gly Ala Leu Leu Lys Pro Ala Lys Pro Phe Met Ser Gln Lys Leu Pro
            165                 170                 175

Phe Leu Leu Tyr Asn Val Gly Pro Phe Ala Phe Glu Pro Thr Cys Pro
            180                 185                 190

Arg

<210> SEQ ID NO 2
<211> LENGTH: 582
<212> TYPE: DNA
<213> ORGANISM: Artificial Sequence
<220> FEATURE:
<223> OTHER INFORMATION: An encoding gene PbrTTS1 of the protein of
      'Dangshan Suli' for promoting the growth of a pollen tube of
      'Dangshan Suli'

<400> SEQUENCE: 2
atgggttctc ctgccgtgtt tgtgcagctc tcagtcctcc tactgagctg cttcactgtc      60
ttcgttcacc caccagccca ctctccggtg cacccaccag cccactctcc ggttcaccca     120
ccaagccccc cccaccacca cggccaccca ccggttcacc ctcctatgta cccacctaag     180
aaacctttcc caaggagctt tgtagcggtt caaggcgtcg tttactgcaa atcttgcaac     240
tactccggcg tcgacaccct aacggcgcc aagccagttc ttggtgctac agtaaagcta     300
cagtgcaaca acagaaagtt cccattggtt gtgaaggaaa ccactgataa aaatggctac     360 tttttttatca cggcacccaa gaccatcacc acctttggag ctcacaagtg caaggtgtca     420
ctcgtctcct ctccctccgc cgcctgctcc aagccgtccg atctgcatgg tggactgagc     480
ggtgctctcc tgaagcctgc gaagccattt atgtcccaga agctcccatt ccttctctac     540
aacgtcggtc cattcgcctt tgagcccaca tgtcctcgtt aa                        582

<210> SEQ ID NO 3
<211> LENGTH: 18
<212> TYPE: DNA
<213> ORGANISM: Artificial Sequence
<220> FEATURE:
<223> OTHER INFORMATION: PbrTTS1 forward primer

<400> SEQUENCE: 3
atgggttctc ctgccgtg                                                    18

<210> SEQ ID NO 4
<211> LENGTH: 23
<212> TYPE: DNA
<213> ORGANISM: Artificial Sequence
<220> FEATURE:
<223> OTHER INFORMATION: PbrTTS1 reverse primer

<400> SEQUENCE: 4
ttaaacgagg acatgtgggc tca                                              23

<210> SEQ ID NO 5
<211> LENGTH: 22
<212> TYPE: DNA
<213> ORGANISM: Artificial Sequence
<220> FEATURE:
<223> OTHER INFORMATION: removing the signal peptide sequence of the
      gene PbrTTS1 forward primer

<400> SEQUENCE: 5
ggatccatgc acccaccagc cc                                               22

```
<210> SEQ ID NO 6
<211> LENGTH: 25
<212> TYPE: DNA
<213> ORGANISM: Artificial Sequence
<220> FEATURE:
<223> OTHER INFORMATION: removing the signal peptide sequence of the
      gene PbrTTS1 forward primer

<400> SEQUENCE: 6
tctagaacga ggacatgtgg gctca                                        25

<210> SEQ ID NO 7
<211> LENGTH: 20
<212> TYPE: DNA
<213> ORGANISM: Artificial Sequence
<220> FEATURE:
<223> OTHER INFORMATION: gene amplifying forward primer

<400> SEQUENCE: 7
tgtcttcgtt cacccaccag                                              20

<210> SEQ ID NO 8
<211> LENGTH: 20
<212> TYPE: DNA
<213> ORGANISM: Artificial Sequence
<220> FEATURE:
<223> OTHER INFORMATION: gene amplifying reverse primer

<400> SEQUENCE: 8
cgctacaaag ctccttggga                                              20

<210> SEQ ID NO 9
<211> LENGTH: 21
<212> TYPE: DNA
<213> ORGANISM: Artificial Sequence
<220> FEATURE:
<223> OTHER INFORMATION: reference gene forward primer

<400> SEQUENCE: 9
tcagtcgccg ccggcctttt g                                            21

<210> SEQ ID NO 10
<211> LENGTH: 19
<212> TYPE: DNA
<213> ORGANISM: Artificial Sequence
<220> FEATURE:
<223> OTHER INFORMATION: reference gene reverse primer

<400> SEQUENCE: 10
tgggctttgc tcctcttac                                               19

<210> SEQ ID NO 11
<211> LENGTH: 22
<212> TYPE: DNA
<213> ORGANISM: Artificial Sequence
<220> FEATURE:
<223> OTHER INFORMATION: removing the signal peptide sequence of the
      gene PbrTTS1 forward primer

<400> SEQUENCE: 11
gaattcatgc acccaccagc cc                                           22

<210> SEQ ID NO 12
<211> LENGTH: 25
<212> TYPE: DNA
<213> ORGANISM: Artificial Sequence
<220> FEATURE:
```

<223> OTHER INFORMATION: removing the signal peptide sequence of the
      gene PbrTTS1 reverse primer

<400> SEQUENCE: 12
ggatccacga ggacatgtgg gctca                                         25

<210> SEQ ID NO 13
<211> LENGTH: 31
<212> TYPE: DNA
<213> ORGANISM: Artificial Sequence
<220> FEATURE:
<223> OTHER INFORMATION: removing the signal peptide sequence of the
      gene PbrS1-RNase forward primer

<400> SEQUENCE: 13
ggatccatgt acgattattt tcaatttacg c                                  31

<210> SEQ ID NO 14
<211> LENGTH: 24
<212> TYPE: DNA
<213> ORGANISM: Artificial Sequence
<220> FEATURE:
<223> OTHER INFORMATION: removing the signal peptide sequence of the
      gene PbrS1-RNase reverse primer

<400> SEQUENCE: 14
gaattgatac tgaacactgg aggg                                          24

<210> SEQ ID NO 15
<211> LENGTH: 27
<212> TYPE: DNA
<213> ORGANISM: Artificial Sequence
<220> FEATURE:
<223> OTHER INFORMATION: removing the signal peptide sequence of the
      gene PbrS2-RNase forward primer

<400> SEQUENCE: 15
gaattcatgg cgagatacga ttatttt                                       27

<210> SEQ ID NO 16
<211> LENGTH: 28
<212> TYPE: DNA
<213> ORGANISM: Artificial Sequence
<220> FEATURE:
<223> OTHER INFORMATION: removing the signal peptide sequence of the
      gene PbrS2-RNase reverse primer

<400> SEQUENCE: 16
agatctatac tgaatatcat caatgggg                                      28

<210> SEQ ID NO 17
<211> LENGTH: 31
<212> TYPE: DNA
<213> ORGANISM: Artificial Sequence
<220> FEATURE:
<223> OTHER INFORMATION: removing the signal peptide sequence of the
      gene PbrS3-RNase forward primer

<400> SEQUENCE: 17
gaattcatgt acgattattt tcaatttacg c                                  31

<210> SEQ ID NO 18
<211> LENGTH: 27
<212> TYPE: DNA
<213> ORGANISM: Artificial Sequence
<220> FEATURE:
<223> OTHER INFORMATION: removing the signal peptide sequence of the gene PbrS3-RNase reverse primer

<400> SEQUENCE: 18
agatctatac ttgatattgt tggtggg                                       27

<210> SEQ ID NO 19
<211> LENGTH: 31
<212> TYPE: DNA
<213> ORGANISM: Artificial Sequence
<220> FEATURE:
<223> OTHER INFORMATION: removing the signal peptide sequence of the
      gene PbrS5-RNase forward primer

<400> SEQUENCE: 19
gaattcatgt acgattattt tcaatttacg c                                  31

<210> SEQ ID NO 20
<211> LENGTH: 27
<212> TYPE: DNA
<213> ORGANISM: Artificial Sequence
<220> FEATURE:
<223> OTHER INFORMATION: removing the signal peptide sequence of the
      gene PbrS5-RNase reverse primer

<400> SEQUENCE: 20
agatctatac ttgatattgt tggtggg                                       27

<210> SEQ ID NO 21
<211> LENGTH: 31
<212> TYPE: DNA
<213> ORGANISM: Artificial Sequence
<220> FEATURE:
<223> OTHER INFORMATION: removing the signal peptide sequence of the
      gene PbrS7-RNase forward primer

<400> SEQUENCE: 21
gaattgatgt acgattattt tcaatttacg c                                  31

<210> SEQ ID NO 22
<211> LENGTH: 23
<212> TYPE: DNA
<213> ORGANISM: Artificial Sequence
<220> FEATURE:
<223> OTHER INFORMATION: removing the signal peptide sequence of the
      gene PbrS7-RNase reverse primer

<400> SEQUENCE: 22
agatctatac ttaacatcgg ccg                                           23

<210> SEQ ID NO 23
<211> LENGTH: 31
<212> TYPE: DNA
<213> ORGANISM: Artificial Sequence
<220> FEATURE:
<223> OTHER INFORMATION: removing the signal peptide sequence of the
      gene PbrS34-RNase forward  primer

<400> SEQUENCE: 23
gaattgatgt acgattattt tcaatttacg c                                  31

<210> SEQ ID NO 24
<211> LENGTH: 28
<212> TYPE: DNA
<213> ORGANISM: Artificial Sequence
<220> FEATURE:
<223> OTHER INFORMATION: removing the signal peptide sequence of the
      gene PbrS34-RNase reverse primer

<400> SEQUENCE: 24
agatctatac tgaatactat tgtttggg					28

<210> SEQ ID NO 25
<211> LENGTH: 244
<212> TYPE: PRT
<213> ORGANISM: Artificial Sequence
<220> FEATURE:
<223> OTHER INFORMATION: DS/1-244

<400> SEQUENCE: 25

```
Met Gly Ser Pro Ala Val Phe Val Gln Leu Ser Val Leu Leu Leu Ser
1               5                   10                  15

Cys Phe Thr Val Phe Gly Asn Val Ile Thr Thr Leu Pro Ala Ser Pro
            20                  25                  30

Pro His His Ser Val His Tyr Ser His Pro Val Ala Ser Pro Thr His
        35                  40                  45

Pro Pro Ala His Pro Pro Thr His Gly Gln His Arg Gln Pro Leu
    50                  55                  60

Pro His Ser Pro Thr Ala Ser Pro Val His Pro Ala His Ser Pro
65                  70                  75                  80

Val His Pro Pro Ala His Ser Pro Val His Pro Pro Ser Pro Pro His
                85                  90                  95

His His Gly His Pro Pro Val His Pro Pro Met Tyr Pro Pro Lys Lys
            100                 105                 110

Pro Phe Pro Arg Ser Phe Val Ala Val Gln Gly Val Val Tyr Cys Lys
        115                 120                 125

Ser Cys Asn Tyr Ser Gly Val Asp Thr Leu Asn Gly Ala Lys Pro Val
    130                 135                 140

Leu Gly Ala Thr Val Lys Leu Gln Cys Asn Asn Arg Lys Phe Pro Leu
145                 150                 155                 160

Val Val Lys Glu Thr Thr Asp Lys Asn Gly Tyr Phe Phe Ile Thr Ala
                165                 170                 175

Pro Lys Thr Ile Thr Thr Phe Gly Ala His Lys Cys Lys Val Ser Leu
            180                 185                 190

Val Ser Ser Pro Ser Ala Ala Cys Ser Lys Pro Ser Asp Leu His Gly
        195                 200                 205

Gly Leu Ser Gly Ala Leu Leu Lys Pro Ala Lys Pro Phe Met Ser Gln
    210                 215                 220

Lys Leu Pro Phe Leu Leu Tyr Asn Val Gly Pro Phe Ala Phe Glu Pro
225                 230                 235                 240

Thr Cys Pro Arg
```

<210> SEQ ID NO 26
<211> LENGTH: 244
<212> TYPE: PRT
<213> ORGANISM: Artificial Sequence
<220> FEATURE:
<223> OTHER INFORMATION: XSJ/1-244

<400> SEQUENCE: 26

```
Met Gly Ser Pro Ala Val Phe Val Gln Leu Ser Val Leu Leu Leu Ser
1               5                   10                  15

Cys Phe Thr Val Phe Gly Asn Val Ile Thr Thr Leu Pro Ala Ser Pro
            20                  25                  30

Pro His His Ser Val His Tyr Ser His Pro Val Ala Ser Pro Thr His
```

```
                35                  40                  45
Pro Pro Ala His Pro Pro Thr His Gly Gln His His Arg Gln Pro Leu
 50                  55                  60
Pro His Ser Pro Thr Ala Ser Pro Val His Pro Ala His Ser Pro
 65                  70                  75                  80
Val His Pro Pro Ala His Ser Pro Val His Pro Pro Ser Pro Pro His
                 85                  90                  95
His His Gly His Pro Pro Val His Pro Pro Met Tyr Pro Pro Lys Lys
                100                 105                 110
Pro Phe Pro Arg Ser Phe Val Ala Val Gln Gly Val Val Tyr Cys Lys
                115                 120                 125
Ser Cys Asn Tyr Ser Gly Val Asp Thr Leu Asn Gly Ala Lys Pro Val
            130                 135                 140
Leu Gly Ala Thr Val Lys Leu Gln Cys Asn Asn Arg Lys Phe Pro Leu
145                 150                 155                 160
Val Val Lys Glu Thr Thr Asp Lys Asn Gly Tyr Phe Phe Ile Thr Ala
                165                 170                 175
Pro Lys Thr Ile Thr Thr Phe Gly Ala His Lys Cys Lys Val Ser Leu
                180                 185                 190
Val Ser Ser Pro Ser Ala Ala Cys Ser Lys Pro Ser Asp Leu His Gly
            195                 200                 205
Gly Leu Ser Gly Ala Leu Leu Lys Pro Ala Lys Pro Phe Met Ser Gln
210                 215                 220
Lys Leu Pro Phe Leu Leu Tyr Asn Val Gly Pro Phe Ala Phe Glu Pro
225                 230                 235                 240
Thr Cys Pro Arg

<210> SEQ ID NO 27
<211> LENGTH: 218
<212> TYPE: PRT
<213> ORGANISM: Artificial Sequence
<220> FEATURE:
<223> OTHER INFORMATION: CG/1-218

<400> SEQUENCE: 27

Met Gly Ser Pro Ala Val Phe Val Gln Leu Ser Val Leu Leu Leu Ser
 1               5                  10                  15
Cys Phe Thr Val Phe Gly Asn Val Ile Thr Thr Leu Pro Ala Ser Pro
                 20                  25                  30
Pro His His Ser Val His Tyr Ser His Pro Val Ala Ser Pro Thr His
                 35                  40                  45
Pro Pro Ala His Ser Pro Val His Pro Ala His Ser Pro Val His
 50                  55                  60
Pro Pro Ser Pro Pro His His His Gly His Pro Val His Pro Pro
 65                  70                  75                  80
Met Tyr Pro Pro Lys Lys Pro Phe Pro Arg Ser Phe Val Ala Val Gln
                 85                  90                  95
Gly Val Val Tyr Cys Lys Ser Cys Asn Tyr Ser Gly Val Asp Thr Leu
                100                 105                 110
Asn Gly Ala Lys Pro Val Leu Gly Ala Thr Val Lys Leu Gln Cys Asn
            115                 120                 125
Asn Arg Lys Phe Pro Leu Val Val Lys Glu Thr Thr Asp Lys Asn Gly
        130                 135                 140
Tyr Phe Phe Ile Thr Ala Pro Lys Thr Ile Thr Thr Phe Gly Ala His
145                 150                 155                 160
```

```
Lys Cys Lys Val Ser Leu Val Ser Ser Pro Ser Ala Ala Cys Ser Lys
                165                 170                 175

Pro Ser Asp Leu His Gly Gly Leu Ser Gly Ala Leu Leu Lys Pro Ala
            180                 185                 190

Lys Pro Phe Met Ser Gln Lys Leu Pro Phe Leu Leu Tyr Asn Val Gly
        195                 200                 205

Pro Phe Ala Phe Glu Pro Thr Cys Pro Arg
    210                 215

<210> SEQ ID NO 28
<211> LENGTH: 244
<212> TYPE: PRT
<213> ORGANISM: Artificial Sequence
<220> FEATURE:
<223> OTHER INFORMATION: XS/1-244

<400> SEQUENCE: 28

Met Gly Ser Pro Ala Val Phe Val Gln Leu Ser Val Leu Leu Leu Ser
1               5                   10                  15

Cys Phe Thr Val Phe Gly Asn Val Ile Thr Thr Leu Pro Ala Ser Pro
            20                  25                  30

Pro His His Ser Val His Tyr Ser His Pro Val Ala Ser Pro Thr His
        35                  40                  45

Pro Pro Ala His Pro Pro Thr His Gly Gln His His Arg Gln Pro Leu
    50                  55                  60

Pro His Ser Pro Thr Ala Ser Pro Val His Pro Ala His Ser Pro
65                  70                  75                  80

Val His Pro Pro Ala His Ser Pro Val His Pro Pro Ser Pro Pro His
                85                  90                  95

His His Gly His Pro Pro Val His Pro Pro Met Tyr Pro Pro Lys Lys
            100                 105                 110

Pro Phe Pro Arg Ser Phe Val Ala Val Gln Gly Val Val Tyr Cys Lys
        115                 120                 125

Ser Cys Asn Tyr Ser Gly Val Asp Thr Leu Asn Gly Ala Lys Pro Val
    130                 135                 140

Leu Gly Ala Thr Val Lys Leu Gln Cys Asn Asn Arg Lys Phe Pro Leu
145                 150                 155                 160

Val Val Lys Glu Thr Thr Asp Lys Asn Gly Tyr Phe Phe Ile Thr Ala
                165                 170                 175

Pro Lys Thr Ile Thr Thr Phe Gly Ala His Lys Cys Lys Val Ser Leu
            180                 185                 190

Val Ser Ser Pro Ser Ala Ala Cys Ser Lys Pro Ser Asp Leu His Gly
        195                 200                 205

Gly Leu Ser Gly Ala Leu Leu Lys Pro Ala Lys Pro Phe Met Ser Gln
    210                 215                 220

Lys Leu Pro Phe Leu Leu Tyr Asn Val Gly Pro Phe Ala Phe Glu Pro
225                 230                 235                 240

Thr Cys Pro Arg

<210> SEQ ID NO 29
<211> LENGTH: 193
<212> TYPE: PRT
<213> ORGANISM: Artificial Sequence
<220> FEATURE:
<223> OTHER INFORMATION: Pbr041309.1/1-193

<400> SEQUENCE: 29
```

Met Gly Ser Pro Ala Val Phe Val Gln Leu Ser Val Leu Leu Leu Ser
1               5                   10                  15

Cys Phe Thr Val Phe Val His Pro Ala His Ser Pro Val His Pro
            20                  25                  30

Pro Ala His Ser Pro Val His Pro Ser Pro Pro His His His Gly
            35                  40                  45

His Pro Pro Val His Pro Pro Met Tyr Pro Pro Lys Lys Pro Phe Pro
    50                  55                  60

Arg Ser Phe Val Ala Val Gln Gly Val Val Tyr Cys Lys Ser Cys Asn
65                  70                  75                  80

Tyr Ser Gly Val Asp Thr Leu Asn Gly Ala Lys Pro Val Leu Gly Ala
                85                  90                  95

Thr Val Lys Leu Gln Cys Asn Asn Arg Lys Phe Pro Leu Val Val Lys
                100                 105                 110

Glu Thr Thr Asp Lys Asn Gly Tyr Phe Phe Ile Thr Ala Pro Lys Thr
                115                 120                 125

Ile Thr Thr Phe Gly Ala His Lys Cys Lys Val Ser Leu Val Ser Ser
130                 135                 140

Pro Ser Ala Ala Cys Ser Lys Pro Ser Asp Leu His Gly Gly Leu Ser
145                 150                 155                 160

Gly Ala Leu Leu Lys Pro Ala Lys Pro Phe Met Ser Gln Lys Leu Pro
                165                 170                 175

Phe Leu Leu Tyr Asn Val Gly Pro Phe Ala Phe Glu Pro Thr Cys Pro
                180                 185                 190

Arg

<210> SEQ ID NO 30
<211> LENGTH: 244
<212> TYPE: PRT
<213> ORGANISM: Artificial Sequence
<220> FEATURE:
<223> OTHER INFORMATION: FS/1-244

<400> SEQUENCE: 30

Met Gly Ser Pro Ala Val Phe Val Gln Leu Ser Val Leu Leu Leu Ser
1               5                   10                  15

Cys Phe Thr Val Phe Gly Asn Val Ile Thr Thr Leu Pro Ala Ser Pro
            20                  25                  30

Ser His His Ser Val His Tyr Ser His Pro Val Ala Ser Pro Thr His
            35                  40                  45

Pro Pro Ala His Pro Pro Thr His Gly Gln His His Arg Gln Pro Leu
    50                  55                  60

Pro His Pro Pro Thr Ala Ser Pro Val His Pro Ala His Ser Pro
65                  70                  75                  80

Val His Pro Pro Ala His Ser Pro Val His Pro Ser Pro Pro His
            85                  90                  95

His His Gly His Pro Pro Val His Pro Pro Met Tyr Pro Pro Lys Lys
                100                 105                 110

Pro Phe Pro Arg Ser Phe Val Ala Val Gln Gly Val Val Tyr Cys Lys
                115                 120                 125

Ser Cys Asn Tyr Ser Gly Val Asp Thr Leu Asn Gly Ala Lys Pro Val
                130                 135                 140

Leu Gly Ala Thr Val Lys Leu Gln Cys Asn Asn Arg Lys Phe Pro Leu
145                 150                 155                 160

```
Val Val Lys Glu Thr Thr Asp Lys Asn Gly Tyr Phe Phe Ile Thr Ala
                165                 170                 175

Pro Lys Thr Ile Thr Thr Phe Gly Ala His Lys Cys Lys Val Ser Leu
            180                 185                 190

Val Ser Ser Pro Ser Ala Ala Cys Ser Lys Pro Ser Asp Leu His Gly
        195                 200                 205

Gly Leu Ser Gly Ala Leu Leu Lys Pro Ala Lys Pro Phe Met Ser Gln
    210                 215                 220

Lys Leu Pro Phe Leu Leu Tyr Asn Val Gly Pro Phe Ala Phe Glu Pro
225                 230                 235                 240

Thr Cys Pro Arg

<210> SEQ ID NO 31
<211> LENGTH: 244
<212> TYPE: PRT
<213> ORGANISM: Artificial Sequence
<220> FEATURE:
<223> OTHER INFORMATION: HH/1-244

<400> SEQUENCE: 31

Met Gly Ser Pro Ala Val Phe Val Gln Leu Ser Val Leu Leu Leu Ser
1               5                   10                  15

Cys Phe Thr Val Phe Gly Asn Val Ile Thr Thr Leu Pro Ala Ser Pro
            20                  25                  30

Ser His His Ser Val His Tyr Ser His Pro Val Ala Ser Pro Thr His
        35                  40                  45

Pro Pro Ala His Pro Pro Thr His Gly Gln His Arg Gln Pro Leu
    50                  55                  60

Pro His Pro Pro Thr Ala Ser Pro Val His Pro Ala His Ser Pro
65                  70                  75                  80

Val His Pro Pro Ala His Ser Pro Val His Pro Ser Pro Pro His
                85                  90                  95

His His Gly His Pro Pro Val His Pro Pro Met Tyr Pro Pro Lys Lys
            100                 105                 110

Pro Phe Pro Arg Ser Phe Val Ala Val Gln Gly Val Val Tyr Cys Lys
            115                 120                 125

Ser Cys Asn Tyr Ser Gly Val Asp Thr Leu Asn Gly Ala Lys Pro Val
    130                 135                 140

Leu Gly Ala Thr Val Lys Leu Gln Cys Asn Asn Arg Lys Phe Pro Leu
145                 150                 155                 160

Val Val Lys Glu Thr Thr Asp Lys Asn Gly Tyr Phe Phe Ile Thr Ala
                165                 170                 175

Pro Lys Thr Ile Thr Thr Phe Gly Ala His Lys Cys Lys Val Ser Leu
            180                 185                 190

Val Ser Ser Pro Ser Ala Ala Cys Ser Lys Pro Ser Asp Leu His Gly
        195                 200                 205

Gly Leu Ser Gly Ala Leu Leu Lys Pro Ala Lys Pro Phe Met Ser Gln
    210                 215                 220

Lys Leu Pro Phe Leu Leu Tyr Asn Val Gly Pro Phe Ala Phe Glu Pro
225                 230                 235                 240

Thr Cys Pro Arg
```

PROTEIN OF 'DANGSHAN SULI' HAVING FUNCTION OF PROMOTING GROWTH OF POLLEN TUBE, ENCODING GENE PBRTTS1 AND USE THEREOF

CROSS REFERENCE TO RELATED APPLICATIONS

This application claims priority to Chinese application number 201810642892.3, the disclosure of which is incorporated by reference herein in its entirety.

FIELD OF THE DISCLOSURE

The disclosure relates generally to the field of plant genetic engineering. More specifically, the disclosure relates to the field of a protein from a plant variety 'Dangshan Suli' for promoting the growth of a pollen tube, a gene PbrTTS1 encoding the protein, and a use thereof.

BACKGROUND

A self-incompatibility (SI) phenomenon is a widespread way of controlling inbreeding in the plant kingdom. The SI mainly includes three types, i.e., sporophytic SI, papaveraceae SI, and S-RNase-based gametophytes SI. Among them, the S-RNase-based SI mainly includes species of Rosaceae, Solanaceae and Plantaginaceae (Clarke and Newbigin 1993; Huang et al. 2009).

The pear belongs to the specie of Rosaceae, and mainly shows the SI phenomenon based on S-RNase. In the SI reaction of the pear, the S-locus genotypes of female and male gametes play a decisive role. When the genotype carried by the male gametophyte and the genotype carried by the female gametophyte are different, the pollen can germinate and grow; and vice versa (Hua et al. 2008). In the mechanism of pear SI, other non-S factors can also affect the process of SI, in addition to the decisive role of the main S-locus genotypes. In tobacco, the secreted proteins, such as 120K, NaTTS and NaPELPIII, in the style stroma affect the process of SI in tobacco.

The 120K, NaTTS, and NaPELPIII are highly-glycosylated proteins of one class that currently have been reported to possibly form a complex with the S-RNase in a pistil to participate in the process of SI (Cruz-Garcia et al. 2005). Among them, 120K was absorbed into pollen tube together with S-RNase, so as to participate in the process of SI (Nathan Hancock et al. 2005; McClure 2006). NaTTS proteins display a top-down concentration gradient in the transmitting tissue, thereby directing the pollen tube to grow downward, or alternatively providing nutrients for the growth of the pollen tube (Wu et al. 1995; Wu et al. 2000). NaPELPIII can bind to the cell wall of the pollen tube in vivo, thereby affecting the growth of the pollen tube (De Graaf et al. 2004; Eberle et al. 2013).

120K, NaTTS, and NaPELPIII all belong to the family of AGPs, which is rich in proline and highly-glycosylated. they contain a conserved Cys-rich C-terminal domain (CTD) and has a glycosylated fragment at the N-terminal (Schultz et al. 2002). However, it is still unclear that whether the conserved C-terminal domain or the N-terminal glycosylated fragment of a gene structure participates in the process of SI.

During the process of pollination and fertilization of pear, whether the pollen can germinate and grow on the stigma and whether it can grow in the style stroma to reach the embryo sac directly affects the success of pollination. There are few reports on a gene controlling the growth of the pollen tube in the pear.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

Some embodiments of the disclosure provide an AGPs family gene that participates in a process of SI. Other embodiments of the disclosure provide a protein from a plant variety 'Dangshan Suli' for promoting the growth of a pollen tube, a gene PbrTTS1 encoding the protein, and a use thereof.

In some embodiments, the disclosure provides a protein from 'Dangshan Suli' for promoting the growth of a pollen tube of 'Dangshan Suli', and the amino acid sequence of the protein is shown in SEQ ID No: 1.

In other embodiments, the disclosure provides a gene PbrTTS1 encoding the protein for promoting the growth of a pollen tube of 'Dangshan Suli', and the nucleotide sequence of the gene PbrTTS1 encoding the protein is shown in SEQ ID No: 2.

In further embodiments, the disclosure provides a primer for amplifying the gene PbrTTS1 encoding the protein, including a forward primer and a reverse primer. The nucleotide sequence of the forward primer is shown in SEQ ID No: 3. The nucleotide sequence of the reverse primer is shown in SEQ ID No: 4.

According to an embodiment, the disclosure provides a method for amplifying the gene PbrTTS1 encoding the protein, including the following steps. (1) extracting a total RNA from materials of leaves, stems or styles of 'Dangshan Suli'; (2) conducting reverse transcription to obtain a cDNA, and (3) performing a PCR reaction with the primer and the cDNA as a template to obtain a PCR reaction product as the gene PbrTTS1 encoding the protein.

Optionally, the PCR reaction system has a volume of 20 μL, and particularly includes components of the following contents: 2 μL of 50 ng/μL cDNA, 6 μL of 2×PCR Master Mix, 1 μL of a 1.0 μmol/L forward primer, 1 μL of a 1 μmol/L reverse primer, and the balance of ddH$_2$O.

Optionally, the procedure of the PCR reaction is as follows: predenaturing at 94° C. for 3 mins, denaturing at 94° C. for 30 s, annealing at 60° C. for 30 s, and extending at 72° C. for 30 s, conducting for 35 thermal cycles, extending at 72° C. for 10 min, and storing at 4° C.

According to another embodiment, the disclosure provides a pollen tube growth promoter, which includes a protein from 'Dangshan Suli'.

Optionally, the concentration of the protein in the promoter is no less than 0.005 μmol/L.

According to a further embodiment, the disclosure provides the use of the protein, the gene PbrTTS1 encoding the protein, the primer or the pollen tube growth promoter in pollination or pollen tube growth.

Optionally, the method of pollinating includes the following steps. (1) Removing stamens from the 'Dangshan Suli' on the day before the big bud stage, to obtain the flower of the 'Dangshan Suli' with the stamens removed. (2) Spraying the protein onto the stigma of the flower of the 'Dangshan Suli' and applying pollen of a non-'Dangshan Suli' variety onto the stigma of the 'Dangshan Suli'. And (3) Bagging the pollinated style with a parchment paper bag and fixing the parchment paper bag.

According to an embodiment, the disclosure provides a method for pollination or pollen tube growth including the step of using a gene PbrTTS1 encoding the protein from 'Dangshan Suli'. The nucleotide sequence of the gene PbrTTS1 encoding the protein is shown in SEQ ID No: 2.

According to another embodiment, the disclosure provides a method for pollination or pollen tube growth including the step of using a primer. The primer includes a forward primer and a reverse primer. The nucleotide sequence of the forward primer is shown in SEQ ID No: 3, and the nucleotide sequence of the reverse primer is shown in SEQ ID No: 4. Optionally, the method for pollination or pollen tube growth including the step of using a primer further includes the steps of (1) removing stamens from a 'Dangshan Suli' on a day before a big bud stage, to obtain a flower of the 'Dangshan Suli' with the stamens removed, (2) spraying a protein onto a stigma of the flower of the 'Dangshan Suli' and applying pollen of a non-'Dangshan Suli' variety onto the stigma of the 'Dangshan Suli', and (3) bagging a pollinated style with a parchment paper bag and fixing the parchment paper bag.

Various embodiments of the disclosure may have one or more of the following effects. The protein from 'Dangshan Suli' for promoting the growth of a pollen tube of 'Dangshan Suli' as provided by the disclosure may have the amino acid sequence of the protein as shown in SEQ ID No: 1. A method may include treating the pollen tube with a pollen cultured with the recombinant protein. The protein may promote the growth of the pollen tube. The protein may expand the regulation mechanism by which a non-S factor participates in the process of SI in the pear. Using the recombinant protein to study the mechanism by which the non-S factor participates in the process of SI may greatly reduce the labor cost and improve the pollination efficiency.

BRIEF DESCRIPTION OF THE DRAWINGS

FIG. 3 is a sequence alignment diagram of the PbrTTS1 in different pear strains.

DETAILED DESCRIPTION

Figure 1:
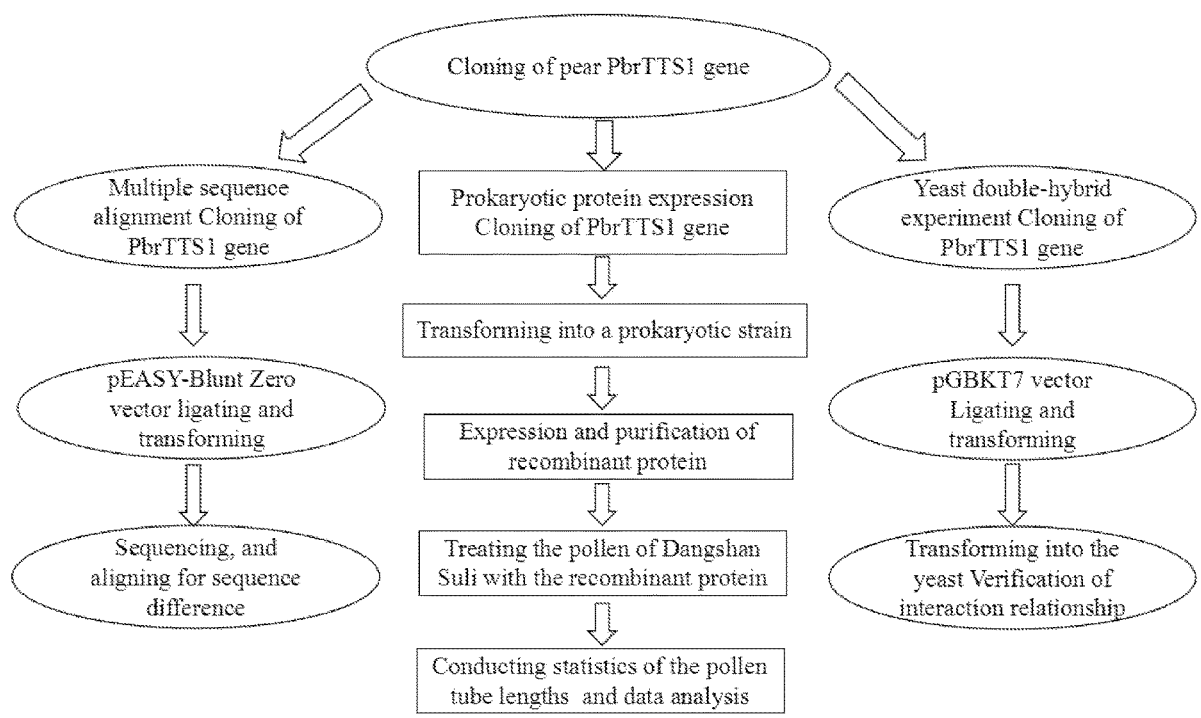
FIG. 1 is a technical flow chart showing an embodiment of the disclosure.

According to an embodiment, the disclosure may provide a protein from 'Dangshan Suli' for promoting the growth of a pollen tube of 'Dangshan Suli', and the amino acid sequence of the protein is shown in SEQ ID No: 1.

According to another embodiment, the disclosure provides a method for preparing the protein from 'Dangshan Suli' for promoting the growth of the pollen tube of the 'Dangshan Suli', including a method for constructing a recombinant prokaryotic expression system and a method for expressing and purifying the recombinant protein.

According to a further embodiment, the disclosure may provide a method for constructing the recombinant prokaryotic expression system may include the following steps.

(1) Adding an ATG and a restriction enzyme cutting site while removing a signal peptide sequence of the gene PbrTTS1 encoding the protein, to obtain a PbrTTS1 gene fragment with the signal peptide removed and a double enzyme digestion site added.

(2) Carrying out double enzyme digestion on the PbrTTS1 gene fragment with the signal peptide removed and a plasmid vector respectively and connecting the two obtained enzyme digestion products to obtain a recombinant plasmid vector PbrTTS1-cutSignalP-pCold-TF.

(3) Transforming the recombinant plasmid vector PbrTTS1-cutSignalP-pCold-TF into a prokaryotic organism for culturing, to obtain candidate prokaryote recombinant expression vectors.

(4) Inoculating the candidate prokaryote recombinant expression vectors into a screening culture medium for culturing, to obtain a bacterial solution.

(5) Carrying out sequencing verification on the bacterial solution. By sequencing, the bacterial solution containing a target gene fragment is the recombinant prokaryotic expression system.

In some embodiments, the method of adding the restriction enzyme cutting site while removing the signal peptide sequence of the gene PbrTTS1 of the pear is to amplify the PbrTTS1 by using the primers PbrTTS1-cutSignalP-F and PbrTTS1-cutSignalP-R, and the obtained amplification product is a PbrTTS1 gene fragment with the signal peptide removed and the double enzyme digestion site added. The nucleotide sequence of the PbrTTS1-cutSignalP-F is shown in SEQ ID No: 5 (5'-ggatccATGCACCCACCAGCCC-3'). The nucleotide sequence of the PbrTTS1-cutSignalP-R is shown in SEQ ID No: 6 (5'-tctagaACGAGGA-CATGTGGGCTCA-3'). The amplification procedure is as follows: predenaturing at 98° C. for 3 s, denaturing at 98° C. for 10 s, annealing at 66° C. for 30 s, extending at 72° C. for 20 s, conducting for 35 thermal cycles, extending at 72° C. for 2 min, and storing at 4° C. The amplification system may be a 50 μL PCR reaction system, which includes 2 μL of a template, 10 μL of a 5×Q5 reaction buffer, 1 μL of 10 mmol/L dNTPs, 0.5 μL of Q5 High-Fidelity DNA Polymerase, 2.5 μL of each 10 μmol/L primer, and a balance of water for achieving 50 μL.

In other embodiments, the plasmid vector is a pCold-TF vector. The enzyme for the double enzyme digestion may be BamH I and Xba I. The disclosure has no specific limitation on the reaction system and procedure for the double enzyme digestion, and enzyme digestion reaction parameters of BamH I and Xba I that are well known in the art can be used. The disclosure has no specific limitation on the connecting method, and a connecting scheme well known in the art can be employed.

In further embodiments, the prokaryotic organism may be *E. coli* Rosetta (DE3). The screening medium may be an LB medium plate containing 100 μg/mL ampicillin. The culturing temperature may be 37° C. The culturing time may be 12-16 h, and preferably 13-15 h.

In one embodiment, the method for expressing and purifying the recombinant protein may include the following steps.

(1) Inoculating the recombinant prokaryotic expression system prepared by the above scheme onto a liquid screening medium for activated culture, and then transferring into a fresh liquid screening culture medium for expanded culture, so as to obtain an expanded-culture bacterial solution.

(2) Adding an inducer into the expanded-culture bacterial solution to induce expression, centrifuging, and collecting a thallus precipitate.

(3) Ultrasonically crushing the thallus precipitate, performing centrifugation, filtering, and collecting a supernatant.

(4) Purifying the pear PbrTTS1 recombinant protein from the supernatant by using a filler for Ni-NTA agarose affinity chromatography.

According to an embodiment, the inoculation amount of the activated culture and the expanded culture may be 1:50. The liquid screening medium may be an LB medium containing 100 μg/ml ampicillin. The activated culture manner may be culturing under shaking at 37° C. and 220 rpm overnight. The expanded culture manner may be culturing under shaking at 37° C. and 200 rpm. The time cut-off for the expanded culture is when OD600 reaches the range of 0.4-0.6 h.

According to another embodiment, the inducer may be IPTG at a final concentration of 0.5 mmol/L. The time for the induced expression may be 24 h. The centrifugal rotation speed may be 12,000 rpm. The centrifugation temperature may be 4° C. The centrifugation time may be 10-30 min. The ultrasound parameters are as follows: opening for 3 s, and then stopping for 7 s, and crushing is conducted until the solution is clear.

According to a further embodiment, the rotation speed of the centrifugation may be 12,000 rpm. Centrifugation time may be 20 min. The pore size of the filtration membrane may be 0.22 μm. The disclosure has no specific limitation on the purifying method using the filler for Ni-NTA agarose affinity chromatography, and a purifying method using the filler for affinity chromatography well known in the art can be used.

Some embodiments of the disclosure may provide a gene PbrTTS1 encoding the protein for promoting the growth of a pollen tube of 'Dangshan Suli', and the nucleotide sequence of the gene PbrTTS1 encoding the protein is shown in SEQ ID No: 2.

Other embodiments of the disclosure may provide a primer for amplifying the gene PbrTTS1 encoding the protein, including a forward primer and a reverse primer. The nucleotide sequence of the forward primer is shown in SEQ ID No: 3 (5'-ATGGGTTCTCCTGCCGTG-3'). The nucleotide sequence of the reverse primer is shown in SEQ ID No: 4 (5'-TTAAACGAGGACATGTGGGCTCA-3').

In some embodiments, the disclosure may provide a method for amplifying the gene PbrTTS1 encoding the protein, including the following steps. (1) Extracting a total RNA from materials of leaves, stems or styles of 'Dangshan Suli'. (2) Conducting reverse transcription to obtain a cDNA. And (3) performing a PCR reaction with the primer and the cDNA as a template to obtain a PCR reaction product as the gene PbrTTS1 encoding the protein.

It should be noted that the disclosure has no specific limitation on the total RNA extraction method, and an extraction method well known in the art can be employed. In embodiments of the disclosure, the total RNA extraction method adopts a plant total RNA extraction kit. The plant total RNA extraction kit is purchased from FOREGENE, and is operated according to the operation instructions provided by the kit.

According to an embodiment, the reverse transcription may be performed using a kit method. The kit method may adopt a TransScript reverse transcription kit. The TransScript reverse transcription kit is purchased from TransGen Biotech Co., Ltd., and is operated according to the operation instructions provided by the kit.

According to another embodiment, the PCR reaction system may be 20 μL, and particularly includes components of the following contents: 2 μL of 50 ng/L cDNA, 6 μL of 2×PCR Master Mix, 1 μL of a 1.0 μmol/L forward primer, 1 μL of a 1 μmol/L reverse primer, and the balance of ddH$_2$O.

According to a further embodiment, the procedure of the PCR reaction may be as follows: predenaturing at 94° C. for 3 min, denaturing at 94° C. for 30 s, annealing at 60° C. for 30 s, and extending at 72° C. for 30 s, conducting for 35 thermal cycles, extending at 72° C. for 10 min, and storing at 4° C.

The disclosure may provide a pollen tube growth promoter, which includes the protein. The concentration of the protein in the promoter may be no less than 0.005 μmol/L, preferably 0.0075-0.1 μmol/L, and more preferably 0.01 μmol/L. The source of the protein may adopt the recombinant protein prepared by the above scheme. The auxiliary material includes an aqueous solution containing 500 mmol/L sodium chloride, 20 mmol/L tris(hydroxymethyl)-aminomethane, and 300 mmol/L imidazole. The pH value of the auxiliary material is 7.9.

According to an embodiment of the disclosure, a method for preparing the promoter may include the following steps: (1) dissolving the aforementioned protein in a solution containing sucrose at a mass concentration of 10%, boric acid at a mass concentration of 0.01%, calcium nitrate at a mass concentration of 0.03%, and 2-morpholineethanesulfonic acid (MES) at a mass concentration of 30 mmol/L, and (2) adjusting the pH with Tris.

The disclosure may provide the use of the protein, the gene PbrTTS1 encoding the protein, the primer or the pollen tube growth promoter in pollination or pollen tube growth.

According to an embodiment of the disclosure, the method of pollinating may include the following steps: (1) removing stamens from the 'Dangshan Suli' on the day before the big bud stage, to obtain the flower of the 'Dangshan Suli' with the stamens removed, (2) spraying the protein onto the stigma of the flower of the 'Dangshan Suli' and applying pollen of a non-'Dangshan Suli' variety onto the stigma of the 'Dangshan Suli', and (3) bagging the pollinated style with a parchment paper bag and fixing the parchment paper bag.

According to a further embodiment of the disclosure, the treatment method for the pollen tube growth is pre-culturing the pollen of the 'Dangshan Suli' with 4 ml of a pear pollen medium for 40 min. The culturing conditions of the pollen is culturing on a shaker at 25° C. and 60 rpm. The pre-cultured pollen is then dispensed into 2 ml EP tubes according to the calculated respective volumes, and the total volume of the added protein and the pre-cultured pollen is 200 L, and three biological replicate experiments are performed for each concentration gradient. The pollen is then incubated on a shaker at 25° C. and 60 rpm for 2 h.

The following describes multiple exemplary embodiments of the disclosure with references to the accompany drawings.

Embodiment 1

Tissue Localization of PbrTTS1 Gene

RNA was extracted from stems, leaves, fruit, pollens and styles of 'the 'Dangshan Suli', and reversely transcribed to obtain a first strand of cDNA for detection of an expression site of PbrTTS1.

Figure 2:
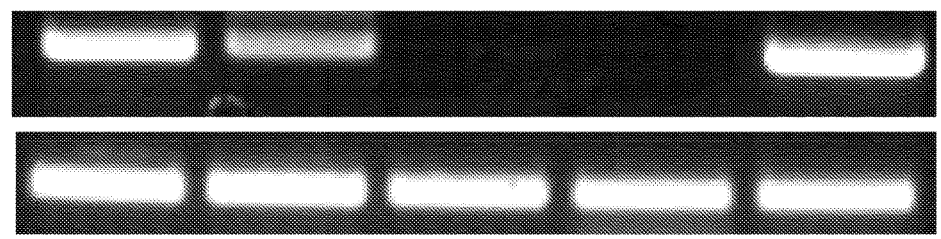
FIG. 2 is a diagram showing the expression situations of the PbrTTS1 gene in various tissues of the pear.

The RNA extraction is conducted using a plant total RNA extraction kit (purchased from FOREGENE and operated according to the operation instructions provided by the kit). The synthesis of the first strand of cDNA was conducted by using a TransScript reverse transcription kit (purchased from TransGen Biotech Co., Ltd., and operated according to the operation instructions provided by the kit). The primer pair for gene amplifying was: PbrTTS1-F1: 5'-TGTCTTCGTT-CACCCACCAG-3' (SEQ ID No: 7). PbrTTS1-R1: 5'-CGC-TACAAAGCTCCTTGGGA-3' (SEQ ID No: 8), and additionally PbrTubulin was used as a reference gene, and the primer pair was PbrTubulin-F: 5'-TCAGTCGCCGCCGGCCTTTTG-3' (SEQ ID No: 9). PbrTubulin-R: 5'-TGGGCTTTGCTCCTCTTAC-3' (SEQ ID No: 10). The reaction system of a 20 µL PCR included 100 ng of cDNA, and 2×Hieff™ PCR Master Mix (available from YeasenBiotechCo., Ltd.). 1.0 µmol/L of the aforementioned primers and sterile water were also included. The PCR reaction was performed on a Veriti amplifier according to the following procedure: predenaturing at 94° C. for 3 min, denaturing at 94° C. for 30 s, annealing at 60° C. for 30 s, extending at 72° C. for 30 s, conducting for 35 thermal cycles, extending at 72° C. for 10 min, and storing at 4° C. The PCR product was detected by 1.5% agarose gel electrophoresis to generate a single PCR band product. The results of the tissue localization experiment showed that, the PbrTTS1 gene was expressed in each of leaves, stems and styles, and was not expressed in pollens and fruit (FIG. 2).

Embodiment 2

Identification of Polymorphism in the PbrTTS1 Gene

RNA was extracted from styles of 'Dangshan Suli', 'Housui', 'Shinseiki', 'Cuiguan', 'Huanghua', and 'Kisui', and reversely transcripted to obtain a first strand of cDNA for cloning of the gene PbrTTS1.

RNA extraction and reverse transcription were carried out in accordance with Embodiment 1. The primer pair for gene amplifying was SEQ ID No: 3 and SEQ ID No: 4. The high-fidelity enzyme for the gene cloning employed Q5 High-Fidelity DNA Polymerase (available from NEB), and the 50 µL PCR reaction system included 2 µL of cDNA, 10 µL of a 5×Q5 Reaction Buffer, 1 µL of 10 mmol/L dNTPs, 0.5 µL of the Q5 High-Fidelity DNA Polymerase, 2.5 µL of each 10 µmol/L primer, and a balance of water for achieving 50 µL. The PCR reaction was performed on a Veriti amplifier according to the following procedure: predenaturing at 98° C. for 3 s, denaturing at 98° C. for 10 s, annealing at 66° C. for 30 s, extending at 72° C. for 20 s, conducting for 35 thermal cycles, extending at 72° C. for 2 min, and storing at 4° C. A single PCR band product was generated.

Figure 3:
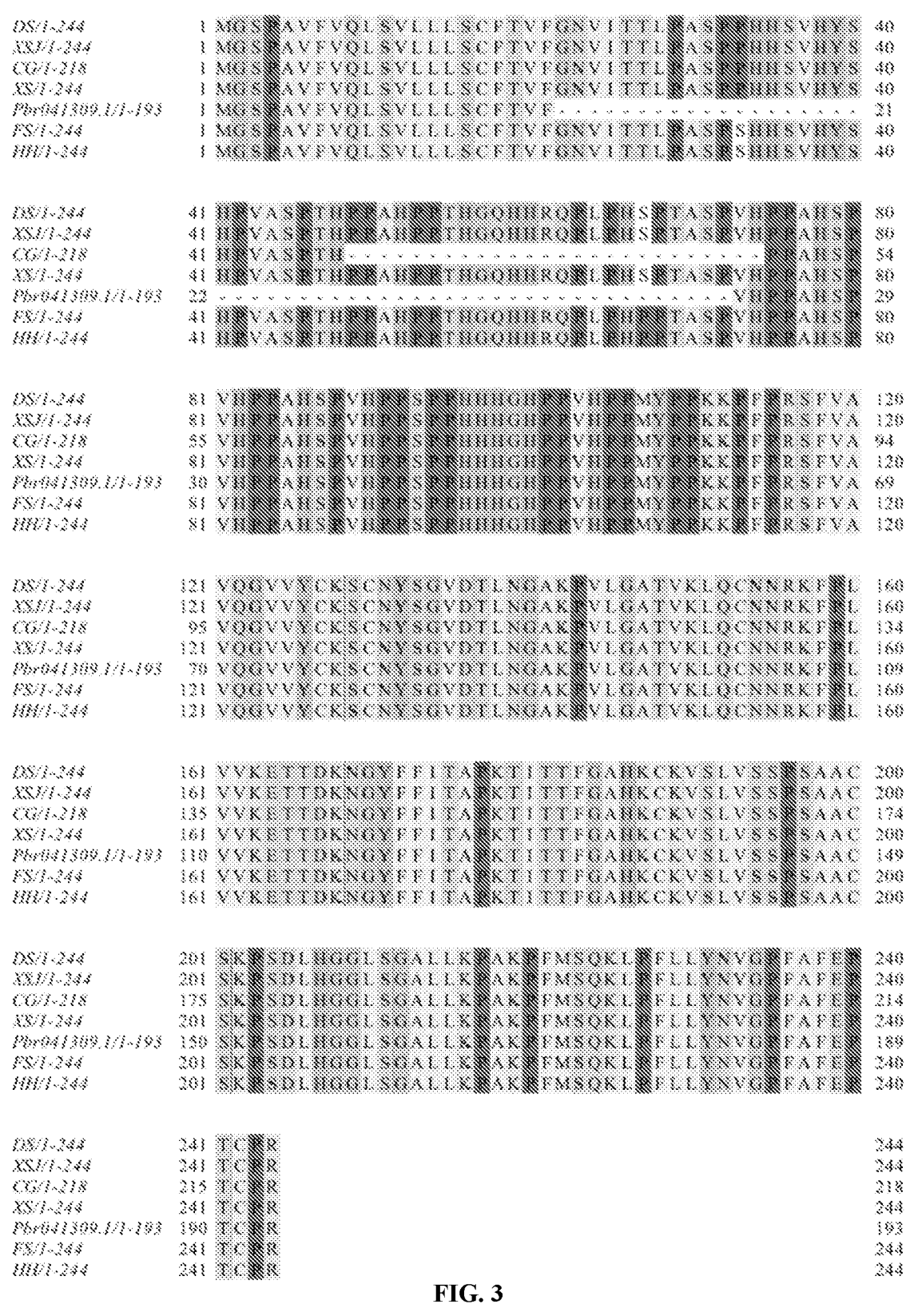

After the PCR product was detected by the 1% agarose gel electrophoresis, the DNA fragments were recovered using a rapid agarose gel DNA recovery kit (purchased from ComWin Biotech Co. Ltd.), and the procedure followed the operation instructions. A ligation reaction was conducted between the recovered and purified DNA solution and a pEASY-Blunt Zero vector (purchased from TransGen Biotech Co., Ltd.) and operated according to the procedure of the instructions. The total volume of the ligation reaction system was 5 µL, including 4.5 µL of the purified PCR product and 0.5 µL of the pEASY-Blunt Zero vector. Ligation was conducted at 25° C. for 10 mins. 5 µL of the ligation product was taken and transformed into E. coli DH5a by a thermal shock method (referring to Molecular Cloning: A Laboratory Manual, the 3rd edition, Science Press, 2002), and screened for positive clones in a LB solid plate containing 100 mg/L kanamycin. 3 positive clones were picked for sequencing (completed by GENEWIZ, Inc. at Suzhou). The sequencing results showed that, the PbrTTS1 had a small amount of differences in amino acids among different pear varieties. The nucleotide sequence of the cloned PbrTTS1 gene was as shown in SEQ ID NO: 1. The analysis of the BLAST results proved that the gene newly obtained from the pear was a member of the AGPs gene family, and this gene was named as PbrTTS1 (FIG. 3). In FIG. 3, 'DS', 'XSJ', 'HH', 'FS', 'XS' and 'CG' respectively represent 'Dangshan Suli', 'Shinseiki', 'Huanghua', 'Housui', 'Kisui' and 'Cuiguan'.

Embodiment 3

Identification of Specific Recognition Between the PbrTTS1 Gene and the PbrS-RNase According to the analysis of multiple cloning sites and vector sequences of a yeast double-hybrid pGADT7 and pGBKT7 vector, the signal peptides and termination codons of PbrTTS1, PbrS1-RNase (AB002139.1), PbrS2-RNase (AB014073.1), PbrS3-RNase (AB002140.1), PbrS5-RNase (AB002141.1), PbrS7-RNase (AB002143.1), and PbrS34-RNase (DQ414813.1) were analyzed and removed. EcoR I and BamH I and their isocaudamers Mfe I and BgL II were selected as endonucleases, primers were designed according to primer design principles (the underlined part is the restriction enzyme cutting site), and the sequences of the primer pair was as shown as follows:

PbrTTS1-pGBKT7-F:
(SEQ ID No: 11)
5'-gaattcATGCACCCACCAGCCC-3'

PbrTTS1-pGBKT7-R:
(SEQ ID No: 12)
5'-ggatccACGAGGACATGTGGGCTCA-3'

PbrS1-RNase-pGADT-F:
(SEQ ID No: 13)
5'-ggatccATGTACGATTATTTTCAATTTACGC-3'

PbrS1-RNase-pGADT7-R:
(SEQ ID No: 14)
5'-gaattgATACTGAACACTGGAGGG-3'

PbrS2-RNase-pGADT7-F:
(SEQ ID No: 15)
5'-gaattcATGGCGAGATACGATTATTTT-3'

PbrS2-RNase-pGADT7-R:
(SEQ ID No: 16)
5'-agatctATACTGAATATCATCAATGGGG-3'

PbrS3-RNase-pGADT7-F:
(SEQ ID No: 17)
5'-gaattcATGTACGATTATTTTCAATTTACGC-3'

PbrS3-RNase-pGADT7-R:
(SEQ ID No: 18)
5'-agatctATACTTGATATTGTTGGTGGG-3'

-continued

PbrS5-RNase-pGADT7-F:
(SEQ ID No: 19)
5'-gaattcATGTACGATTATTTTCAATTTACGC-3'

PbrS5-RNase-pGADT7-R:
(SEQ ID No: 20)
5'-agatctATACTTGATATTGTTGGTGGG-3'

PbrS7-RNase-pGADT7-F:
(SEQ ID No: 21)
5'-gaattgATGTACGATTATTTTCAATTTACGC-3'

PbrS7-RNase-pGADT7-R:
(SEQ ID No: 22)
5'-agatctATACTTAACATCGGCCG-3'

PbrS34-RNase-pGADT7-F:
(SEQ ID No: 23)
5'-gaattgATGTACGATTATTTTCAATTTACGC-3'

PbrS34-RNase-pGADT7-R:
(SEQ ID No: 24)
5'-agatctATACTGAATACTATTGTTTGGG-3'

The plasmid extracted from the preserved bacterial solution having the correct sequencing was used as a template of PbrTTS1, and the cloning of a gene containing the restriction enzyme cutting site was conducted by using the styles of 'Cuiguan', 'Huanghua' and 'Dangshan Suli' as the template of PbrS-RNase. The annealing temperature for PCR amplification was 59° C., and the PCR reaction system and amplification procedure were the same as those of Embodiment 2. The band of interest was recovered and ligated onto the pGBKT7 and pGADT7 vectors, so as to construct respective recombinant vectors. The total volume of the double enzyme digestion system was 40 μL. The double enzyme digestion system included 15 μL of a corresponding purified PCR product, 4 μL of 10×FastDigest Green Buffer (purchased from ThermoFisher), 2 μL of each of respective enzymes, and 17 μL of water. The total volume of the double enzyme digestion system of the pGADT7 and pGBKT7 vectors was 40 μL. The double enzyme digestion system contained 10 μL of the corresponding vector DNA obtained by plasmid extraction, 4 μL of 10×FastDigest Green Buffer, 2 μL of EcoR I, 2 μL of BamH I (purchased from ThermoFisher), and 22 μL of water. It was recovered after enzyme digestion at 37° C. for 3-4 hours (with the same method as that of Embodiment 1). The expression vector pGBKT7, which was digested by the restriction endonuclease was ligated to the PbrTTS1 gene using a T4 DNA ligase (purchased from NEB) at 4° C. for 16 hours, with the total reaction volume being 10 μL. The reaction contained 1 μL of a 10×T4 DNA Ligase Buffer, 1 μL of the T4 DNA ligase, 6 μL of double-enzyme-digestion recovery products of the PbrTTS1 gene, and 2 μL of double-enzyme-digestion recovery products of the pGADT7 vector. PbrS-RNase and pGADT7 were ligated in the same way. 10 μL of the ligation product was taken and transformed into the E. coli competent DH5a, and screened for positive clones respectively in a LB solid plate containing 100 μg/ml of kanamycin and a LB solid plate containing 100 μg/ml of ampicillin, respectively. Plasmids were extracted for enzyme digestion and PCR identification. The sequencing results confirmed that there was no mutation in the reading frame, and a recombinant vector containing an inserted target fragment was obtained.

Figure 4:
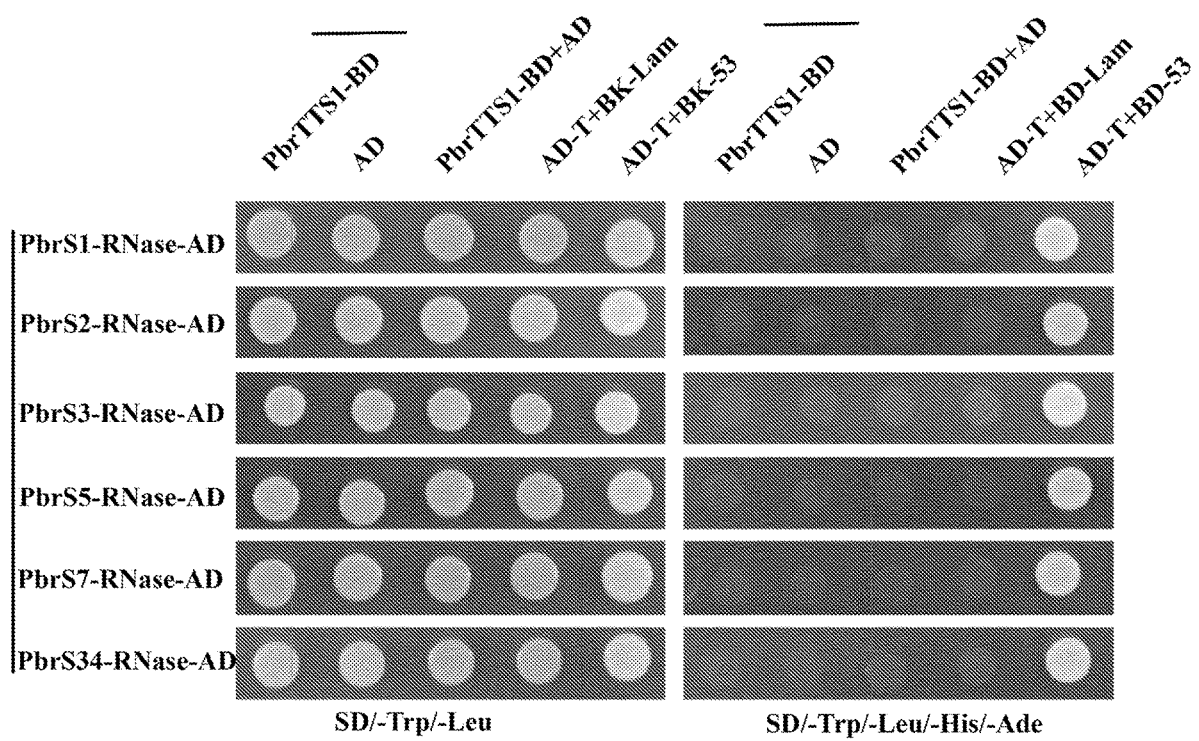
FIG. 4 is a verification diagram of the interaction relationship between PbrTTS1 and PbrS-RNase.

The plasmid extraction was carried out according to the procedure of the plasmid extraction instructions provided by the ComWin Biotech Co. Ltd. The extracted plasmid PbrTTS1-BD was combined with PbrS1-RNase-AD, PbrS2-RNase-AD, PbrS3-RNase-AD, PbrS5-RNase-AD, PbrS7-RNase-AD, and PbrS34-RNase-AD, respectively. PbrTTS1-BD+AD and BD were combined with PbrS1-RNase-AD, PbrS2-RNase-AD, PbrS3-RNase-AD, PbrS5-RNase-AD, PbrS7-RNase-AD, and PbrS34-RNase-AD, respectively. pGADT7-T+pGBKT7-53 and pGADT7-T+pGBKT7-Lam were respectively co-transferred into a yeast competent strain AH109 (Shanghai Weidi Biotechnology Co., Ltd.). The yeast transformation was carried out according to the instructions. Plates coated with SD/-Trp/-Leu were cultured at 28° C. for 2-3 days. Monoclonal colonies of each combination were streaked onto the SD/-Trp/-Leu and SD/-Trp/-Leu/-Ade/-His plates respectively, and continually cultured at 28° C. for 2-3 days to observe their growth state on the two types of plates, thereby determining an interaction relationship. Thereafter, the monoclonal colonies were cultured in 4 ml of a SD/-Trp/-Leu liquid medium on a shaker at 28° C. and 220 rpm, until the OD value reached about 0.8. 5 μL of a corresponding bacterial solution was pipetted and dropped onto the two types of plates, i.e., the SD/-Trp/-Leu and SD/-Trp/-Leu/-Ade/-His plates, and continually cultured at 28° C. Thereafter, the photographs were taken with a canon camera, and the photographs were treated by Adobe Photoshop CS6 (FIG. 4). In FIG. 4, AD, BD, AD-T, BD-53 and BD-Lam respectively represent pGADT7, pGBKT7, pGADT7-T, pGBKT7-53 and pGBKT7-Lam, the horizontal and vertical line parts indicate that the PbrTTS1-BD and the BD are respectively combined with 6 kinds of PbrS-RNases, and the other three columns are the same combination in different groups of experiments.

The experimental results showed that, there was no phenomenon of specific binding between PbrTTS1 and different PbrS-RNases, such that the PbrTTS1 cannot specifically recognize a certain type of PbrS-RNase to specifically participate in the process of SI.

Embodiment 4

Construction of Protein Expression of PbrTTS1

Figure 5:
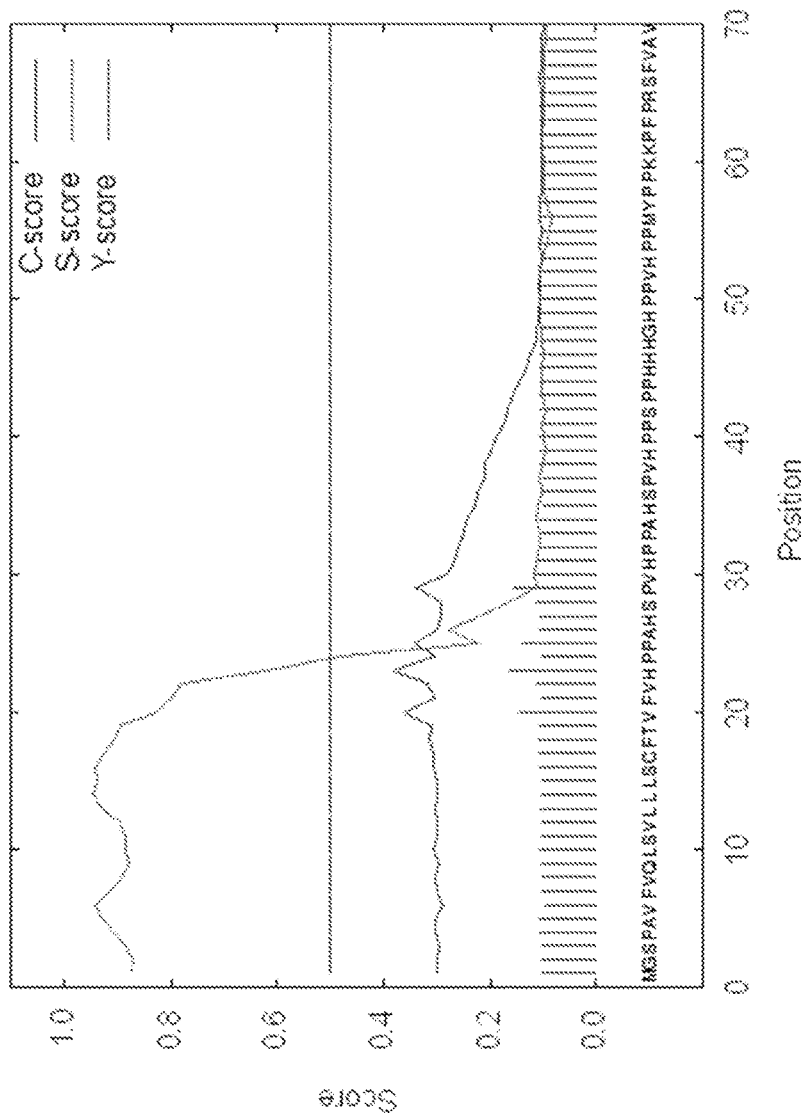
FIG. 5 is a prediction diagram of the signal peptide of SEQ ID No: 2 in the disclosure.

According to the analysis of the multiple cloning sites on the pCold-TF vector and the restriction enzyme cutting sites on the coding region sequence of the PbrTTS1 gene, as shown in FIG. 5, the signal peptide sequence of the pear PbrTTS1 gene was analyzed and removed, and BamH I and Xba I were selected as endonucleases. Primers carrying restriction enzyme cutting sites (the underlined part was the restriction enzyme cutting site) were designed using a Primer 5.0 software according to a general primer designing principle, and the sequences of the primer pair were as shown as follows:

PbrTTS1-cutSignalP-F:
(SEQ ID No: 5)
5'-ggatccATGCACCCACCAGCCC-3'

PbrTTS1-cutSignalP-R:
(SEQ ID No: 6)
5'-tctagaACGAGGACATGTGGGCTCA-3'

The PCR reaction system and amplification procedure were the same as those of Embodiment 2. The band of interest was recovered and then ligated to the pCold-TF vector, so as to construct a recombinant vector PbrTTS1-cutSignalP-pCold-TF. The process of ligating the double enzyme digestion reaction system and the vector was the same as that of Embodiment 3, and the recombinant vector S7-cutSignalP-pCold-TF was obtained.

Figure 6:
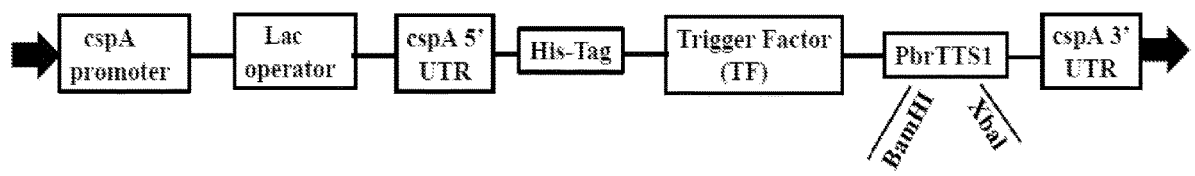
FIG. 6 is a schematic flow chart of constructing a carrier according to Embodiment 4 of the disclosure.

1 ng of the recombinant expression vector S7-cutSignalP-pCold-TF was taken and transformed into *E. coli* Rosetta (DE3), coated onto a plate containing 100 μg/mL of ampicillin for screening of a recombinant gene, incubated in a 37° C. incubator for 12-16 h to obtain the recombinant gene of PbrTTS1-cutSignalP-pCold-TF (FIG. 6).

Colonies were selected for sequencing to obtain positive colonies. The colonies tested as positive were picked and inoculated into 4 ml of a LB liquid medium containing ampicillin (100 μg/ml), and cultured under shaking at 37° C. and 220 rpm overnight. One single colony was randomly selected for streak culture, and a small amount of grown streak culture bacteria was inoculated in 1 ml of a LB (containing 100 μg/ml of ampicillin) liquid medium, cultured under shaking at 37° C. and 220 rpm for 12 h, then added with 300 μL of sterilized 50% glycerol per 700 μL of the bacterial solution, mixed well, and then quickly frozen with liquid nitrogen and stored in a refrigerator at −80° C. to obtain the recombinant expression strain of PbrTTS1-cutSignalP-pCold-TF.

Embodiment 5

Expression and Purification of PbrTTS1 Recombinant Protein

The PbrTTS1 recombinant expression strain prepared above was inoculated into 10 ml of the LB (containing 100 μg/ml of ampicillin) liquid medium at a ratio of 1:50, and cultured under shaking at 37° C. and 220 rpm overnight to activate the recombinant expression strain. The activated recombinant expression strain was then transferred into 300 ml of the LB medium (containing 100 μg/mL of ampicillin) at a ratio of 1:50 for culturing under culturing conditions of 37° C. and 220 rpm, the activated recombinant expression strain was cultured under shaking until the OD600 was 0.4-0.6, and then 5 ml of the bacterial solution was taken out as a negative control. It was quickly placed onto ice for 5 mins, then placed into a shaker at 15° C. and allowed to stand therein for 40 min, and finally added with IPTG at a final concentration of 0.5 mmol/L to induce expression for 24 hours. After the expression was completed, the thallus precipitate was collected by centrifuging at 4° C. and 12,000 rpm, and at this point 5 ml of the induced thallus precipitate was taken out. The thallus was resuspended with PBS and then crushed ultrasonically at a power of 240 W under the following conditions: opening for 3 s, and then stopping for 7 s, and the crushing was conducted until the solution was clear. After the ultrasonic crushing was completed, the solution was centrifuged at 4° C. and 12,000 rpm for 20 mins, the supernatant was filtered by a filter membrane of 0.22 m to remove impurities, and the supernatant was collected. The control protein pCold-TF was also expressed according to the aforementioned method.

Figure 7:
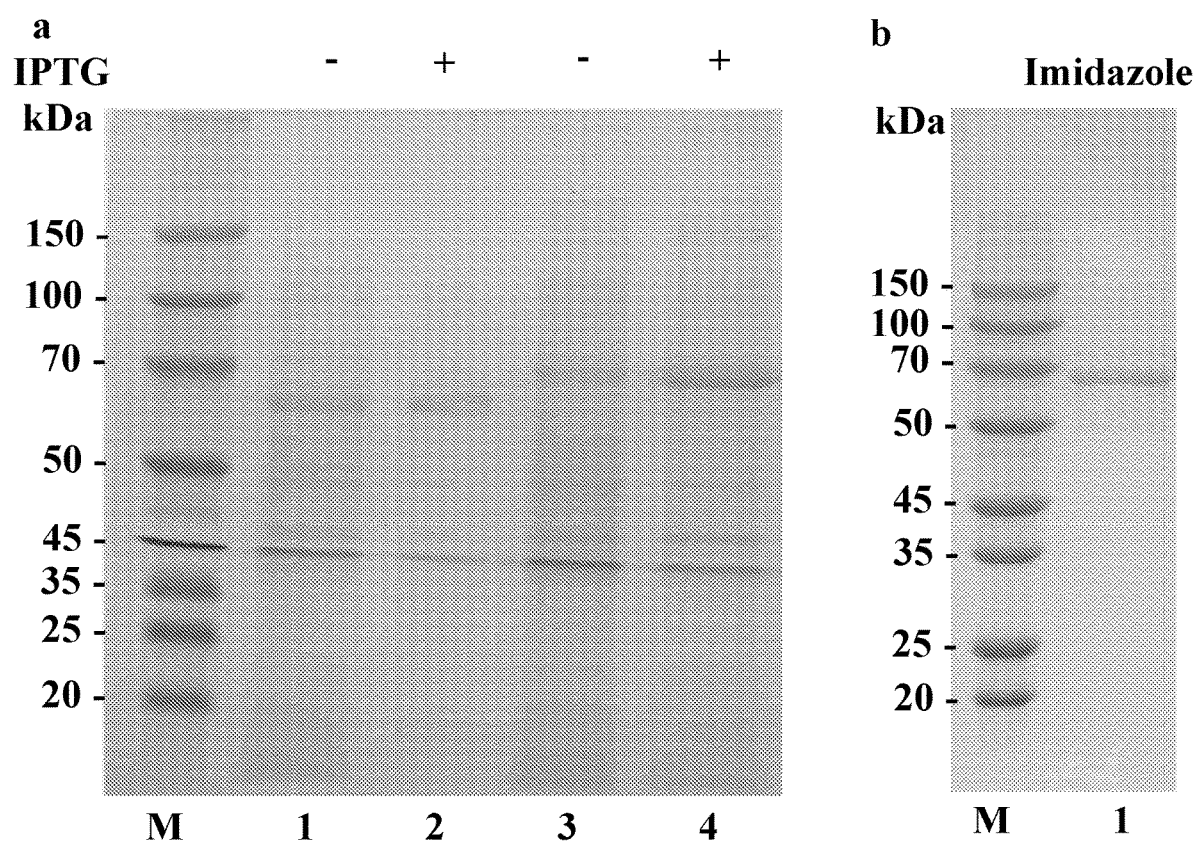
FIG. 7 shows the SDS-PAGE detection of expression and purification of a PbrTTS1 recombinant protein.

The sediment and negative control were each added with 200 μL of 10% SDS, mixed well and then placed in a water bath of boiling water at 100° C. for 10 min, cooled in ice for 2 min, and then centrifuged at 4° C. and 12,000 rpm for 10 min. 20 μL of each supernatant was taken and added with 5 μL of a 5×protein loading buffer (purchased from Sangon Biotech). Then L was taken, and subjected to 12% conventional SDS-PAGE electrophoresis, Coomassie brilliant blue staining and decoloring to detect the expression situation of the recombinant protein. In FIG. 7, FIG. 7-*a* is a SDS-PAGE detection diagram of the expression of PbrTTS1 and pCold-TF recombinant proteins. M represents Marke, 1 and 2 respectively represent that the pCold-TF recombinant protein is induced with and without IPTG, and 3 and 4 respectively represent that the PbrTTS 1 recombinant protein is induced with and without IPTG. FIG. 7-*b* is a SDS-PAGE detection diagram of purification of the PbrTTS1 recombinant protein. M represents Marke, and 1 represents the PbrTTS1 recombinant protein after being eluted in imidazole and concentrated. As shown in FIG. 7-*a*, the expression situation of the two recombinant proteins after induced with the addition of IPTG was shown. Lanes 2 and 4 respectively showed that the target protein was expressed in the thallus after the IPTG was added for induction.

The pear PbrTTS1 recombinant protein was purified by using a filler for Ni-NTA agarose affinity chromatography (purchased from Fcmacs Biotech Co., Ltd.). The specific operation was as follows: the aforementioned filler was balanced with a PBS buffer (140 mmol/L of sodium chloride, 2.7 mmol/L of potassium chloride, 10 mmol/L of disodium hydrogen phosphate, 1.8 mmol/L of potassium dihydrogen phosphate, pH 7.9) having a volume that was 10 times greater than that of the filler, at a controlled flow rate of 1 ml/min. The protein supernatant obtained after being filtered through the filter membrane passed through a purification column at a controlled flow rate of 1 ml/min. The column was flushed with a washing liquid containing 20 mmol/L of imidazole (500 mmol/L of sodium chloride, 20 mmol/L of tris(hydroxymethyl)aminomethane, 20 mM of imidazole, pH 7.9) having a volume that was 20 times greater than that of the filler, at a controlled flow rate of 1 ml/min. The purification column was eluted with an elution buffer containing 300 mmol/L of imidazole (500 mmol/L of sodium chloride, 20 mmol/L of tris(hydroxymethyl)aminomethane, 300 mmol/L of imidazole, pH 7.9) having a volume that was 10 times greater than that of the column, at a controlled flow rate of 1 ml/min, the eluent was collected to obtain the purified protein, and the purified protein was concentrated and desalted by using an ultrafiltration tube. 20 μl of the purified protein was taken and added with 5 μl of the 5×protein loading buffer (purchased from Sangon Biotech), and then L was taken and subjected to the 12% conventional SDS-PAGE electrophoresis, Coomassie brilliant blue staining and decoloring to detect the purification situation of the recombinant protein. As shown in FIG. 7-*b*, the band of the purified PbrTTS1 recombinant protein is relatively single, indicating that it contains relatively fewer impurity proteins.

The purified protein was subjected to spin dialysis at 4° C. for 24 hours by flowing in a pollen medium (10% of sucrose, 0.01% of boric acid, 0.03% of calcium nitrate, 30 mM of 2-morpholineethanesulfonic acid (MES), with the pH value of 6.2, and the pH was adjusted by Tris) at the ratio of 1:1000, and then placed under −80° C. and ready for use.

Embodiment 6

Identification of Pollen Tube Growth by the PbrTTS1 Recombinant Protein

Figure 8:
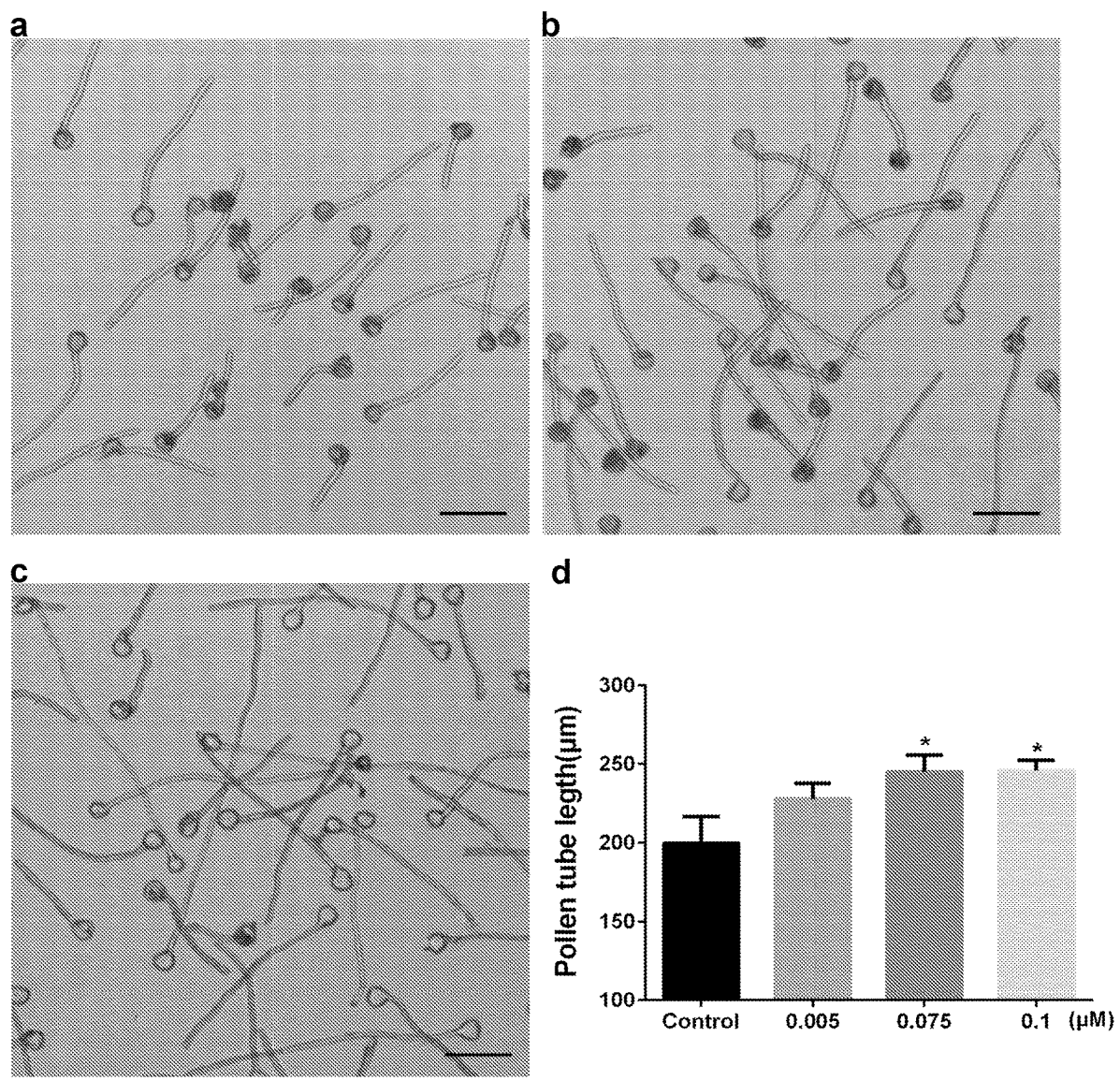
FIG. 8 shows the effect of the PbrTTS1 recombinant protein on the pollen tube growth of 'Dangshan Suli' and length statistics of the pollen tube.

The pollen of the 'Dangshan Suli' was treated with the aforementioned dialyzed PbrTTS1 recombinant protein according to different concentration gradients. The concentration gradients of the PbrTTS1 recombinant protein were set as four concentration gradients, i.e., a control (0), 0.005 μmol/L, 0.075 μmol/L and 0.01 μmol/L respectively. The specific experimental method was as follows:

First, the pollen of 'Dangshan Suli' was pre-cultured with 4 ml of a pear pollen medium for 40 min. The culturing conditions of the pollen was culturing on a shaker at 25° C. and 60 rpm. The formulation of the pollen medium was as that of Embodiment 4. The pre-cultured pollen was then dispensed into 2 ml EP tubes according to the calculated respective volumes, and the total volume of the added protein and the pre-cultured pollen was 200 μL, and three biological replicate experiments were performed for each concentration gradient. The pollen was then incubated on a shaker at 25° C. and 60 rpm for 2 hours. The cultured pollen was photographed by using a NiKON ECLIPSE E100 microscope (FIG. 8-a, FIG. 8-b, and FIG. 8-c). In FIG. 8, FIG. 8-a is a control, FIGS. 8-b and 8-c show the treatment of the pollen of the 'Dangshan Suli' with different concentrations of the PbrTTS 1 recombinant protein, respectively, and FIG. 8-d shows the length statistics of the pollen tube.

The statistics of the lengths of the pollen tubes were conducted by using an IPWin32 software. The statistics of about 30 pollen tubes were conducted for each concentration gradient, and the average value and standard error of three replicates were calculated (FIG. 8-d). The experimental results showed that, by treating the pollen of the 'Dangshan Suli' with different concentrations of the PbrTTS1 recombinant protein, the PbrTTS1 exhibited a promoting effect on the growth of the pollen of 'Dangshan Suli'.

Various embodiments of the disclosure may have one or more of the following effects. An exemplary method may include treating the pollen tube with a pollen cultured with the recombinant protein. A protein from 'Dangshan Suli' and/or a gene PbrTTS1 encoding the protein may promote the growth of the pollen tube. The protein from 'Dangshan Suli' and/or a gene PbrTTS1 encoding the protein may expand the regulation mechanism by which a non-S factor participates in the process of SI in the pear. Using the recombinant protein to study the mechanism by which the non-S factor participates in the process of SI may greatly reduce the labor cost and improve the pollination efficiency.

The foregoing descriptions are only exemplary implementation manners of the present invention. It should be noted that for a person of ordinary skill in the art, several improvements and modifications may further be made without departing from the principle of the present invention. These improvements and modifications should also be deemed as falling within the protection scope of the present invention.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Not all steps listed in the various figures need be carried out in the specific order described.

The disclosure claimed is:

1. A pollen tube growth promoter, comprising a protein, sodium chloride, tris(hydroxymethyl)aminomethane, and imidazole, wherein the amino acid sequence of the protein is shown in SEQ ID No: 1.

2. The pollen tube growth promoter according to claim 1, wherein the concentration of the protein in the promoter is no less than 0.005 μmol/L.

3. The pollen tube growth promoter according to claim 1, wherein the nucleotide sequence of the gene encoding the protein is shown in SEQ ID No: 2.

4. A method for pollination or pollen tube growth, comprising the step of spraying the protein of the pollen tube growth promoter according to claim 1 onto a stigma of a flower.

5. The method according to claim 4, comprising the steps of:
(1) removing stamens from a plant variety 'Dangshan Suli' to obtain a flower of the 'Dangshan Suli' with the stamens removed;
(2) spraying the protein onto a stigma of the flower of the 'Dangshan Suli' and applying pollen of a non-'Dangshan Suli' variety onto the stigma of the 'Dangshan Suli'; and
(3) bagging a pollinated style with a parchment paper bag and fixing the parchment paper bag.

6. The method according to claim 4, comprising the step of spraying the protein of the pollen tube growth promoter onto the stigma of the flower, wherein the protein is encoded by a gene as shown in SEQ ID No: 2.

7. The pollen tube growth promoter according to claim 1, wherein the pollen tube growth promoter comprises 500 mmol/L sodium chloride, 20 mmol/L tris(hydroxymethyl)aminomethane, and 300 mmol/L imidazole.

* * * * *